(12) United States Patent
Akle et al.

(10) Patent No.: US 10,071,124 B2
(45) Date of Patent: Sep. 11, 2018

(54) TREATMENT OF POST-TRAUMATIC STRESS DISORDER WITH ISOLATED MYCOBACTERIUM

(71) Applicant: IMMODULON THERAPEUTICS LIMITED, London (GB)

(72) Inventors: Charles Akle, London (GB); John Grange, London (GB)

(73) Assignee: IMMODULON THERAPEUTICS LIMITED, London (GB)

( * ) Notice: Subject to any disclaimer, the term of this patent is extended or adjusted under 35 U.S.C. 154(b) by 0 days.

(21) Appl. No.: 14/429,697

(22) PCT Filed: Sep. 17, 2013

(86) PCT No.: PCT/GB2013/052430
§ 371 (c)(1),
(2) Date: Mar. 19, 2015

(87) PCT Pub. No.: WO2014/045023
PCT Pub. Date: Mar. 27, 2014

(65) Prior Publication Data
US 2015/0246080 A1    Sep. 3, 2015

(30) Foreign Application Priority Data
Sep. 20, 2012 (GB) .................................. 1216800.1

(51) Int. Cl.
| | | |
|---|---|---|
| A61K 39/04 | (2006.01) | |
| C12N 1/20 | (2006.01) | |
| A61K 35/74 | (2015.01) | |
| A61K 39/00 | (2006.01) | |

(52) U.S. Cl.
CPC .............. *A61K 35/74* (2013.01); *A61K 39/04* (2013.01); *C12N 1/20* (2013.01); *A61K 2039/58* (2013.01)

(58) Field of Classification Search
CPC .... A61K 2039/58; A61K 35/74; A61K 39/04; C12N 1/20
See application file for complete search history.

(56) References Cited

U.S. PATENT DOCUMENTS

2009/0304749 A1* 12/2009 Stanford ................ A61K 39/04
424/248.1

FOREIGN PATENT DOCUMENTS

WO    WO 01/82939 A    11/2001

OTHER PUBLICATIONS von Reyn et al (AIDS, 24:675-685, 2010).*
Schmidt et al (Brain, Behavior and Immunity, 24:1097-1104, 2010.*
Zovkic et al (Neuropsychopharmacology Reviews, 38:77-93, 2013).*
Van der Staay et al (Behavioral and Brain Functions, 5:11, 2009).*
Pomerantz (Psychiatric Times, Apr. 1, 2006).*
Goswami et al (Frontiers in Neuroscience, 7, Article 89, May 2013).*
International Search Report for PCT/GB2013/052430, dated Jan. 7, 2014, 12 pgs.
Lowry et al., "Identification of an immune-responsive mesolimbocortical serotonergic system: potential role in regulation of emotional behavior", Neuroscience 146, pp. 756-772 (2007).
Matthews et al., "Ingestion of *Mycobacterium vaccae* decreases anxiety-related behavior and improves learning in mice", Behavioural Processes 96, pp. 27-35 (2013).
Schmidt et al., "Chronic psychosocial stress promotes systemic immune activation and the development of inflammatory Th cell responses", Brain, Behavior, and Immunity 24, pp. 1097-1104 (2010).
English Translation of Notice of Reason for Rejection dated Mar. 15, 2016 for JP Application No. 2015-532500; 3 pages.
International Journal of Psychiatry in Clinical Practice, 2009, vol. 13, No. SUPPL. 1, pp. 7. Abstract No. SO 0201; Downloaded Jan. 2016.
Martenyi eta l., "Fluoxetine in the acute treatment and relapse prevention of combat-related post-traumatic stress disorder: Analysis of the veteran group of a placebo-controlled, randomized clinical trial", *European Neuropsychopharmacology*, 2006, 16(5), pp. 340-349.
Stoddard et al., "A Randomized Controlled Trial of Sertraline to Prevent Posttraumatic Stress Disorder in Burned Children", *Journal of Child and Adolescent Psychopharmacology*, 2011, 21(5), pp. 469-477.
Yuksel et al., "Mycobacetrial Strains that Stimulate the Immune System Most Efficiently as Candidates for the Treatment of Bladder Cancer", Journal of Molecular Microbiology and Biotechnology, J Mol Microbial Biotechnol 2011;20:24-28. DOI: 10.1159/000324331 (2011).
DSM-5 Collection, "Posttraumatic Stress Disorder", American Psychiatric Association, 2013, 2 pages, pp. 1-2.
Gill et al., "PTSD is associated with an excess of inflammatory immune activities", Perspectives in Psychiatric Care vol. 45, No. 4, Oct. 2009.

(Continued)

*Primary Examiner* — Padmavathi Baskar
(74) *Attorney, Agent, or Firm* — Squire Patton Boggs (US) LLP

(57) ABSTRACT

The present invention relates to treatment or prevention of post-traumatic stress disorder (PTSD). In particular, the present invention relates to an isolated *Mycobacterium*, for use in the prevention of PTSD and the symptoms associated with such a disorder. Also provided are methods of improving resilience in a subject by administering a therapeutically effective amount of isolated *Mycobacterium*.

12 Claims, 3 Drawing Sheets

(56) References Cited

OTHER PUBLICATIONS

Lindqvist et al., "Proinflammatory milieu in combat-related PTSD is independent of depression and early life stress", Brain, Behavior, and Immunity xxx (2014) xxx-xxx. http://dx.doi.org/10.1016/j.bbi.2014.06.003.
Lowry et al., "The Microbiota, Immunoregulation, and Mental Health: Implications for Public Health", Curr Envir Health Rpt (2016) 3:270-286. DOI 10.1007/s40572-016-0100-5.
Reber et al., "Chronic subordinate colony housing paradigm: A mouse model for mechanisms of PTSD vulnerability, targeted prevention, and treatment—2016 Curt Richter Award Paper", Psychoneuroendocrinology 74 (2016) 221-230.
Reber et al., "Immunization with a heat-killed preparation of the environmental bacterium *Mycobacterium vaccae* promotes stress resilience in mice", PNAS PLUS www.pnas.org/cgi/doi/10.1073/pnas.1600324113.
Turisch et al., "Association of trauma exposure with proinflammatory activity: a transdiagnostic meta-analysis", Transl Psychiatry (2014) 4, e413; doi:10.1038/tp.2014.56.
T. Pace and C. Heim, "A short review on the a short review on the psychoneuroimmunology of posttraumatic stress disorder: from risk factors to medical comorbidities", Brain, Behavior, and Immunity 25 (2011) 6-13.
Uschold-Schmidt et al., "Chronic psychosocial stress results in sensitization of the HPA axis to acute heterotypic stressors despite a reduction of adrenal in vitro ACTH responsiveness", Psychoneuroendocrinology (2012) 37, 1676-1687.

\* cited by examiner

TREATMENT OF POST-TRAUMATIC STRESS DISORDER WITH ISOLATED MYCOBACTERIUM

CROSS-REFERENCE TO RELATED APPLICATIONS

This application is the National Stage of International Patent Application No. PCT/GB2013/052430, filed Sep. 17, 2013, which claims the benefit of GB Application No. 1216800.1, filed Sep. 20, 2012, each of which is incorporated by reference in its entirety.

FIELD OF THE INVENTION

The present invention relates to prevention of post-traumatic stress disorder (PTSD). In particular, the present invention relates to an isolated *Mycobacterium*, for use in the prevention of PTSD and the symptoms associated with such a disorder. Also provided are methods of improving resilience in a subject by administering a therapeutically effective amount of isolated *Mycobacterium*.

BACKGROUND OF THE INVENTION

Anxiety disorders are the most commonly occurring disorders of the psychiatric illnesses and constitute an immense economic burden. In addition to generalised anxiety disorder, they encompass post-traumatic stress disorder (PTSD), panic disorder, obsessive compulsive disorder and social as well as other phobias.

PTSD can be severe and chronic, with some studies suggesting a lifetime prevalence of 1.3% to 7.8% in the general population. PTSD affects about 7.7 million American adults, but it can occur at any age, including childhood. Women are more likely to develop PTSD than men, and there is some evidence that susceptibility to the disorder may run in families. PTSD is often accompanied by depression, substance abuse, or one or more of the other anxiety disorders. PTSD typically follows a psychologically distressing traumatic event. These events may include military combat, terrorist incidents, physical assault, sexual assault, motor vehicle accidents, and natural disasters, for example. The response to the event can involve intense fear, helplessness, or horror. Most people recover from the traumatic event with time and return to normal life. In contrast, in PTSD victims, symptoms persist and may worsen with time, preventing a return to normal life. PTSD studies have reported evidence of increased inflammatory activity in the immune system, including higher levels of inflammatory cytokines both at baseline and following antigenic stimulation. These higher levels of inflammatory activity have been linked to HPA axis abnormalities and to alteration to serotonergic and noradrenergic metabolism. A chronically activated inflammatory response has been shown to exert adverse reactions on many body systems. Specifically, elevations of interleukin-6 (IL-6) have been associated with reports of chronic pain, arthritis, diabetes, cardiovascular disease, and other medical conditions that have been associated with PTSD. Indeed, patients with chronic PTSD have been shown to have significantly higher levels of IL-1$\beta$, IL-6, IL-8, TNF-alpha, and MCP-1, but in some cases lower C-reactive protein and lower soluble CD-40.

Psychotherapy is currently the backbone of PTSD treatment. Methods include cognitive-behavioural therapy, exposure therapy, and eye movement desensitization and reprocessing. Medication can enhance the effectiveness of psychotherapy. Selective serotonin reuptake inhibitors (SSRIs), such as sertraline (Zoloft®) and paroxetine (Paxil®), are the only medications approved for treating PTSD by the Food and Drug Administration. Many unwanted side-effects are associated with SSRI usage. These include concerns about drug interactions, gastrointestinal side-effects, sexual side-effects, suicidal ideation, acute anxiogenic effects, and slow onset of action. Some tricyclic antidepressants (TCAs) and monamine oxidase inhibitors (MAOIs) appear to have some efficacy but patient tolerance is low due to the high incidence of side-effects. MAOIs have dietary restriction requirements and are linked to hypertensive events. TCAs have anticholinergic and cardiovascular side-effects. Lamotrigine, a sodium channel blocker, has had some efficacy in treating PTSD in a small-scale placebo controlled study.

There is a need for the development of treatments or preventative therapies for PTSD that are safe and effective.

SUMMARY OF THE INVENTION

In a first aspect of the invention, there is an isolated *Mycobacterium* for use in the prevention of PTSD and the symptoms associated with such a disorder.

In a second aspect of the invention, there is an isolated *Mycobacterium*, for administration to a subject to prevent the subject's levels of inflammatory markers, including for example IL-6, from being elevated following exposure to a traumatic event or to prevent alteration to serotonergic and noradrenergic metabolisms.

The present invention overcomes the deficiency in the prior art by providing a safe, better tolerated and effective method for preventing PTSD. Surprisingly, the present invention results in a balanced immunoregulatory enhancing effect, with a reduction of inappropriate inflammatory responses. This multi-faceted profile of action cannot be achieved by intervention of a single pathway and so results in a more controlled and effective response compared to the prior art.

DESCRIPTION OF THE DRAWINGS

The invention is described with reference to the following drawings, in which.

DETAILED DESCRIPTION OF THE INVENTION

Figure 1:
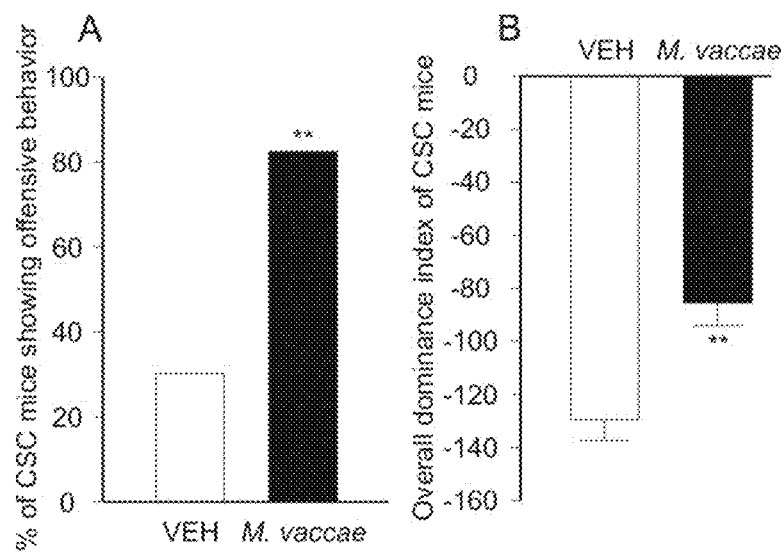
FIG. 1 shows the effect of treatment with *M. vaccae* on proactive behaviour and total dominance index during colony housing.

The present invention utilises mycobacteria, for the treatment or prevention of PTSD.

As used herein, the terms "patient" and/or "subject" can be used interchangeably. For the avoidance of doubt, the present invention is intended preferably for use in humans, however non-human vertebrate animals (Veterinary use) can also be subject to the treatment or preventative therapy. For example horses and dogs are often used in military or police operations as well as in other instances, such as on racetracks, where they may become exposed to traumatic conditions. The therapy of the invention can therefore be of use to restore performance in such animals.

As used herein, the term "preventing" refers to any manner in which at least one sign, symptom, or symptom cluster of a disease or disorder is beneficially altered so as to prevent or delay the onset, retard the progression, prevent relapse, or ameliorate the symptoms or associated symptoms of the disease or disorder. For example, in PTSD, preventing the disorder can, in certain embodiments, prevent the occurrence of at least one of a sign, symptom, and symptom cluster of PTSD.

The present invention also relates to the treatment of PTSD, or one or more symptoms of PTSD, in a subject. Treatment may retard progression, prevent relapse, or ameliorate PTSD, or one or more symptoms of the disorder.

As used herein the phrase "diagnosed with post-traumatic stress disorder (PTSD)" refers to having a sign, symptom, or symptom cluster indicative of PTSD, a psychiatric disorder triggered by a traumatic event. Non-limiting examples of such traumatic events include military combat, terrorist incidents, physical assault, sexual assault, motor vehicle accidents, and natural disasters.

The Diagnostic and Statistical Manual of Mental Disorders-IV-Text revised (DSM-IV-TR), a handbook for mental health professionals that lists categories of mental disorders and the criteria, classifies PTSD as an anxiety disorder. According to the DSM-IV-TR, a PTSD diagnosis can be made if:

(1) the patient experienced, witnessed, or was confronted with an event or events that involved actual or threatened death or serious injury, or a threat to the physical integrity of self or others and the response involved intense fear, helplessness, or horror; (2) as a consequence of the traumatic event, the patient experiences at least 1 re-experiencing/intrusion symptom, 3 avoidance/numbing symptoms, and 2 hyper-arousal symptoms, and the duration of the symptoms is for more than 1 month; and (3) the symptoms cause clinically significant distress or impairment in social, occupational, or other important areas of functioning.

In certain embodiments, if the patient's disorder fulfils DSM-IV-TR criteria, the patient is diagnosed with PTSD. In certain embodiments, if the patient has at least one sign, symptom, or symptom cluster of PTSD, the patient is diagnosed with the disorder. In certain embodiments, a scale is used to measure a sign, symptom, or symptom cluster of PTSD-, and the disorder is diagnosed on the basis of the measurement using that scale. In certain embodiments, a "score" on a scale is used to diagnose or assess a sign, symptom, or symptom cluster of PTSD. In certain embodiments, a "score" can measure at least one of the frequency, intensity, or severity of a sign, symptom, or symptom cluster of PTSD.

As used herein, the term "symptom" and "symptoms" refer to subjective indications that characterize a disorder. Symptoms of PTSD may refer to, for example, but not limited to recurrent and intrusive trauma recollections, recurrent and distressing dreams of the traumatic event, acting or feeling as if the traumatic event were recurring, distress when exposed to trauma reminders, physiological reactivity when exposed to trauma reminders, efforts to avoid thoughts or feelings associated with the trauma, efforts to avoid activities or situations, inability to recall trauma or trauma aspects, markedly diminished interest in significant activities, feelings of detachment or estrangement from others, restricted range of affect, sense of a foreshortened future, social anxiety, anxiety with unfamiliar surroundings, difficulty falling or staying asleep, irritability or outbursts of anger, difficulty concentrating, hyper-vigilance, problems with pain perception, pain tolerance, and exaggerated startle response. In certain embodiments, potentially threatening stimuli can cause hyper-arousal or anxiety. In certain embodiments, the physiological reactivity manifests in at least one of abnormal respiration, abnormal cardiac rate of rhythm, abnormal blood pressure, abnormal function of a special sense, and abnormal function of sensory organ. In certain embodiments, restricted range of effect characterized by diminished or restricted range or intensity of feelings or display of feelings can occur and sense of a foreshortened future can manifest in thinking that one will not have a career, marriage, children, or a normal life span. In certain embodiments, children and adolescents may have symptoms of PTSD such as, for example and without limitation, disorganized or agitated behaviour, repetitive play that expresses aspects of the trauma, frightening dreams which lack recognizable content, and trauma-specific re-enactment. In certain embodiments, a symptom can be stress associated with memory recall.

As used herein, the term "symptom cluster" refers to a set of signs, symptoms, or a set of signs and symptoms, which are grouped together because of their relationship to each other or their simultaneous occurrence. For example, in certain embodiments PTSD is characterized by three symptom clusters: re-experiencing/intrusion, avoidance/numbing, and hyper-arousal.

As used herein, the term "re-experiencing/intrusion" refers to at least one of recurrent and intrusive trauma recollections, recurrent and distressing dreams of the traumatic event, acting or feeling as if the traumatic event were recurring, distress when exposed to trauma reminders, and physiological reactivity when exposed to trauma reminders. In certain embodiments, the physiological reactivity manifests in at least one of abnormal respiration, abnormal cardiac rate of rhythm, abnormal blood pressure, abnormal function of a special sense, and abnormal function of sensory organ.

As used herein, the term "avoidance/numbing" refers to at least one of efforts to avoid thoughts or feelings associated with the trauma, efforts to avoid activities or situations, inability to recall trauma or trauma aspects, markedly diminished interest in significant activities, feelings of detachment or estrangement from others, restricted range of affect, and sense of a foreshortened future. Restricted range of effect characterized by diminished or restricted range or intensity of feelings or display of feelings can occur. A sense of a foreshortened future can manifest in thinking that one will not have a career, marriage, children, or a normal life span. Avoidance/numbing can also manifest in social anxiety and anxiety with unfamiliar surroundings.

As used herein, the term "hyper-arousal" refers to at least one of difficulty falling or staying asleep, irritability or outbursts of anger, difficulty concentrating, hyper-vigilance, and exaggerated startle response. Potentially threatening stimuli can cause hyper-arousal or anxiety.

As used herein, the term "significantly" refers to a set of observations or occurrences that are too closely correlated to be attributed to chance. For example, in certain embodiments, "significantly changes", "significantly reduces", and "significantly increases" refers to alterations or effects that are not likely to be attributed to chance. In certain embodiments, statistical methods can be used to determine whether an observation can be referred to as "significantly" changed, reduced, increased, or altered.

Patients diagnosed with PTSD may feel "on guard", uneasy, and intensely anxious. Depression, anxiety, panic attacks, and bipolar disorder are often associated with PTSD. Alcohol and drug abuse are also common. In certain embodiments, disorders comorbid with PTSD can include for example but without limitation depression, alcohol and drug abuse.

As used herein, the phrase "improving resilience" refers to increasing the ability of a patient to experience a traumatic event without suffering PTSD or with less post-event symptomatology or disruption of normal activities of daily living. In certain embodiments, improving resilience can, in certain embodiments, reduce at least one of the signs, symptoms, or symptom clusters of PTSD.

In certain embodiments the re-experiencing/intrusion comprises at least one of recurrent and intrusive trauma recollections, recurrent and distressing dreams of the traumatic event, acting or feeling as if the traumatic event were recurring, distress when exposed to trauma reminders, and physiological reactivity when exposed to trauma reminders.

In certain embodiments the physiological reactivity comprises at least one of abnormal respiration, abnormal cardiac rate of rhythm, abnormal blood pressure, abnormal function of at least one special sense, and abnormal function of at least one sensory organ.

In certain embodiments the at least one special sense is selected from sight, hearing, touch, smell, taste, and sense. In certain embodiments the at least one sensory organ is selected from eye, ear, skin, nose, tongue, and pharynx.

In certain embodiments the avoidance/numbing comprises at least one of efforts to avoid thoughts or feelings associated with the trauma, efforts to avoid activities or situations, inability to recall trauma or trauma aspects, markedly diminished interest in significant activities, feelings of detachment or estrangement from others, restricted range of affect, sense of a foreshortened future, social anxiety, and anxiety associated with unfamiliar surroundings.

In certain embodiments the hyper-arousal comprises at least one of difficulty falling or staying asleep, irritability or outbursts of anger, difficulty concentrating, hyper-vigilance, exaggerated startle response, and anxiety from potentially threatening stimuli.

In certain embodiments the isolated *Mycobacterium* does not reduce the physical ability of the patient to respond appropriately and promptly to the potentially threatening stimuli.

In certain embodiments the isolated *Mycobacterium* reduces the difficulty of staying asleep by reducing stress associated with memory recall and dreaming.

In certain embodiments the patient is a child or an adolescent.

In certain embodiments the isolated *Mycobacterium* prevents at least one sign or symptom of the PTSD in the patient, wherein the sign or symptom is selected from disorganized or agitated behaviour, problems with pain perception and pain tolerance, headache, difficult falling or staying asleep, repetitive play that expresses aspects of the trauma, frightening dreams which lack recognizable content, and trauma-specific re-enactment.

In certain embodiments the isolated *Mycobacterium* reduces the incidence of at least one disorder comorbid with PTSD selected from drug abuse, alcohol abuse, and depression in the patient.

In certain embodiments the isolated *Mycobacterium* is administered to the patient before or immediately after a traumatic event.

In certain embodiments the isolated *Mycobacterium* reduces the incidence of at least one sign, symptom, or symptom cluster of PTSD as diagnosed or assessed with at least one of Clinician-Administered PTSD Scale (CAPS), Clinician-Administered PTSD Scale Part 2 (CAPS-2), Clinician-Administered PTSD Scale for Children and Adolescents (CAPS-CA), Impact of Event Scale (IES), Impact of Event Scale-Revised (IES-R), Clinical Global Impression Scale (CGI), Clinical Global Impression Severity of Illness (CGI-S), Clinical Global Impression Improvement (CGI-I), Duke Global Rating for PTSD scale (DGRP), Duke Global Rating for PTSD scale Improvement (DGRP-I), Hamilton Anxiety Scale (HAM-A), Structured Interview for PTSD (SI-PTSD), PTSD Interview (PTSD-I), PTSD Symptom Scale (PSS-I), Mini International Neuropsychiatric Interview (MINI), Montgomery-Asberg Depression Rating Scale (MADRS), Beck Depression Inventory (BDI), Hamilton Depression Scale (HAM-D), Revised Hamilton Rating Scale for Depression (RHRSD), Major Depressive Inventory (MDI), Geriatric Depression Scale (GDS-30), and Children's Depression Index (CDI).

In certain embodiments the isolated *Mycobacterium* significantly changes or reduces a score on at least one of CAPS, CAPS-2, CAPS-CA, IES, IES-R, CGI, CGI-S, CGI-I, DGRP, DGRP-I, HAM-A, SI-PTSD, PTSD-I, PSS-I, MADRS, BDI, HAM-D, RHRSD, MDI, GDS-30, and CDI.

In certain embodiments the isolated *Mycobacterium* significantly reduces an endpoint score compared to a baseline score on at least one of CAPS, CAPS-2, IES, IES-R, and HAMA. In certain embodiments the isolated *Mycobacterium* significantly increases the proportion of responders on the CGI-I having a CGI-I score of at least one of 1 (very much improved) and 2 (much improved). In certain embodiments the isolated *Mycobacterium* increases the proportion of responders on the DGRP-I having a DGRP-I score of at least one of 1 (very much improved) and 2 (much improved).

In certain embodiments an overall score of at most 65 on at least one of the CAPS and the CAP-2 is indicative of prevention of PTSD.

In certain embodiments an overall score of at most 18 on HAM-A is indicative of prevention of anxiety disorder.

In certain embodiments a score of at most 3 on at least one of the CGI-I and the DGRP-I is indicative of prevention of PTSD.

In a further embodiment, the isolated *Mycobacterium* prevents and/or reduces low-grade inflammation concomitant with PTSD. Such low-grade inflammation may be indicated by elevated serum levels of C-reactive protein, such as greater than 3 mg/liter.

In a yet further embodiment, the isolated *Mycobacterium* prevents and/or reduces the incidence of histological damage associated with PTSD and/or concomitant inflammation, such as the colon or other parts of the gastrointestinal tract.

In one embodiment, administration, as defined herein, includes the administration of the isolated *Mycobacterium* in multiple aliquots and/or doses and/or on separate occasions. Preferably the isolated *Mycobacterium* is administered before and continued to be administered to the patient after a traumatic event occurs. More preferably, the isolated *Mycobacterium* is continued to be administered to the patient after a traumatic event occurs.

In one aspect of the present invention the isolated *Mycobacterium* comprises heat-killed *Mycobacterium*. Preferred mycobacterial species for use in the present invention include *M. vaccae, M. thermoresistibile, M. flavescens, M. duvalii, M. phlei, M. obuense, M. parafortuitum, M.*

*sphagni, M. aichiense, M. rhodesiae, M. neoaurum, M. chubuense, M. tokaiense, M. komossense, M. aurum, M. indicus pranii, M. tuberculosis, M. microti; M. africanum; M. kansasii, M. marinum; M. simiae; M. gastri; M. non-chromogenicum; M. terrae; M. triviale; M. gordonae; M. scrofulaceum; M. paraffinicum; M. intracellulare; M. avium; M. xenopi; M. ulcerans; M. diemhoferi, M. smegmatis; M. thamnopheos; M. flavescens; M. fortuitum; M. peregrinum; M. chelonei; M. paratuberculosis; M. leprae; M. lepraemurium* and combinations thereof.

Preferably, the heat-killed *Mycobacterium* is non-pathogenic. The non-pathogenic heat-killed *Mycobacterium* is preferably selected from *M. vaccae, M. obuense, M. parafortuitum, M. aurum, M. indicus pranii, M. phlei* and combinations thereof. More preferably the non-pathogenic heat-killed *Mycobacterium* is a rough variant. The amount of isolated *Mycobacterium* administered to the patient is sufficient to elicit a protective immune response in the patient such that it prevents at least one sign or symptom of the PTSD in the patient, wherein the sign or symptom is selected from disorganized or agitated behaviour, problems with pain perception and pain tolerance, headache, difficult falling or staying asleep, repetitive play that expresses aspects of the trauma, frightening dreams which lack recognizable content, and trauma-specific re-enactment. Preferably, administration of an effective amount of isolated *Mycobacterium* is one which prevents at least one symptom cluster of the PTSD in the patient, wherein the symptom cluster is selected from re-experiencing/intrusion, avoidance/numbing, and hyper-arousal.

In certain embodiments of the invention, it is preferable that a particular dosage of isolated *Mycobacterium* be administered to a subject. Thus, in certain embodiments of the invention, there is provided a containment means comprising the effective amount of heat-killed *Mycobacterium* for use in the present invention, which typically may be from $10^3$ to $10^{11}$ organisms, preferably from $10^4$ to $10^{10}$ organisms, more preferably from $10^6$ to $10^{10}$ organisms, and even more preferably from $10^6$ to $10^9$ organisms per unit dose. The effective amount of heat-killed *Mycobacterium* for use in the present invention may be from $10^3$ to $10^{11}$ organisms, preferably from $10^4$ to $10^{10}$ organisms, more preferably from $10^6$ to $10^{10}$ organisms, and even more preferably from $10^6$ to $10^9$ organisms. Most preferably the amount of heat-killed *Mycobacterium* for use in the present invention is from $10^7$ to $10^9$ cells or organisms. Typically, the composition according to the present invention may be administered at a dose of from $10^8$ to $10^9$ cells for human and animal use. Alternatively the dose is from 0.01 mg to 1 mg or 0.1 mg to 1 mg organisms presented as either a suspension or dry preparation.

In one embodiment there is provided an isolated *Mycobacterium*, for administration to a patient to reduce the elevation of the patient's levels of inflammatory cytokines such as IL-6 following exposure to a traumatic event.

In another embodiment, there is provided an isolated *Mycobacterium*, for administration to a patient to prevent the patient's levels of inflammatory cytokines such as IL-6 or IL-1β or IL-8 or TNF-alpha or MCP-1 from becoming elevated following exposure to a traumatic event. The *Mycobacterium* reduces the elevation of the patient's levels of IL-6 or IL-1β or IL-8, TNF-alpha or MCP-1, following exposure to a traumatic event.

In another embodiment there is provided an isolated *Mycobacterium*, for administration to a patient to prevent the patient's levels of C-reactive protein or soluble CD-40 lowering, following exposure to a traumatic event.

In a further embodiment, the isolated *Mycobacterium* produces an immunomodulatory effect, wherein the ratio of inflammatory to regulatory cytokines present in the plasma of a subject, is maintained at below about 1, respectively. Such inflammatory cytokines include the likes of IL-6, TNF and interferon-gamma, whereas regulatory cytokines include the likes of IL-10 and TGF-beta.

The term "combination" as used throughout the specification, is meant to encompass the administration of the therapeutic agents in the same or separate pharmaceutical formulations, and at the same time or at different times. Thus, an isolated *Mycobacterium* and the pharmaceutical agent may be provided as separate medicaments for administration at the same time or at different times. Preferably, an isolated *Mycobacterium* and pharmaceutical agent are provided as separate medicaments for administration at different times. When administered separately and at different times, either an isolated *Mycobacterium* or pharmaceutical agent may be administered first; however, it is preferable to administer an isolated *Mycobacterium* followed by pharmaceutical agent. In addition, both drugs can be administered in the same day or at different days, and they can be administered using the same schedule or at different schedules during the treatment cycle.

Preferably, the isolated *Mycobacterium* is administered to the patient before any anticipated traumatic event.

Dose delays and/or dose reductions and schedule adjustments are performed as needed depending on individual patient tolerance to treatments.

Before any anticipated traumatic event, effective amounts of *Mycobacterium* may be administered in multiple (repeat) doses, for example two or more, three or more, four or more, five or more, ten or more, or twenty or more repeat doses, at intervals of about 2 weeks, or about 4 weeks or about 8 weeks.

The isolated *Mycobacterium* may be administered to the patient via the parenteral, oral, sublingual, nasal or pulmonary route. In a preferred embodiment, the isolated *Mycobacterium* is administered via a parenteral route selected from subcutaneous, intradermal, subdermal, intraperitoneal, intravenous and intravesicular injection. More preferably, administration by the parenteral route does not comprise injection of mycobacterial cell wall extract.

In another preferred embodiment, the isolated *Mycobacterium* is administered orally, including by suspension, tablets and the like. Liquid formulations could be administered by inhalation of lyophilized or aeorosolized microcapsules. Additional pharmaceutical vehicles could be used to control the duration of action of the preparation. They could be entrapped in microcapsules prepared by coacervation techniques or by interfacial polymerization (hydroxymethylcellulose or gelatin microcapsules) in colloidal drug delivery systems (for example, liposomes, albumin microspheres, micro-emulsions, nanoparticles and nanocapsules) or in macro-emulsions. Excipients, for example, salts, various bulking agents, additional buffering agents, chelating agents, antioxidants, cosolvents and the like can be included in the final formulation.

A suitable dosage schedule according to this embodiment includes administration of the isolated *Mycobacterium* followed by further doses of said isolated *Mycobacterium* 2 weeks later and continuing every 2 weeks for the next 3 doses followed by 4 weeks without treatment. Thereafter, patients may receive the isolated *Mycobacterium* every 4 weeks for up to 12 months or longer following the first dose given. Alternatively, dosing may involve weekly administration following the priming or initial dose.

The patient who is to be exposed to an anticipated traumatic event, according to the present invention, may do so simultaneously, separately or sequentially with administration of the isolated *Mycobacterium*. Preferably the isolated *Mycobacterium* is administered to the patient prior to the anticipated traumatic event. More specifically, the isolated *Mycobacterium* may be administered to the patient between about 4 weeks and 1 week prior to any anticipated traumatic event. Preferably, the isolated *Mycobacterium* may be administered as one or more aliquots each containing an effective amount of the isolated *Mycobacterium* which may be administered at one or more time intervals between 4 weeks and 1 week prior to any anticipated traumatic event. Even more preferably, the isolated *Mycobacterium* may be administered as one or more aliquots each containing an effective amount of the isolated *Mycobacterium* which may be administered at one or more time intervals between 4 weeks and 1 week before any anticipated traumatic event and/or the isolated *Mycobacterium* may be administered, and repeated on at least about 2, 4, 6, 8, 10, 12, 15, 20 or more occasions before and/or after any anticipated traumatic event.

In one embodiment of the present invention, the isolated *Mycobacterium* may be in the form of a medicament administered to the patient in a dosage form and/or in a schedule as set out in the examples.

In an aspect of the invention, the effective amount of the isolated *Mycobacterium* may be administered as a single dose. Alternatively, the effective amount of the isolated *Mycobacterium* may be administered in multiple (repeat) doses, for example two or more, three or more, four or more, five or more, ten or more, or twenty or more repeat doses. Preferably, the isolated *Mycobacterium* is administered between about 4 weeks and 1 day prior to an anticipated traumatic event, more preferably between about 4 weeks and 1 week, or about between 3 weeks and 1 week, or about between 3 weeks and 2 weeks. Administration may be presented in single or multiple doses.

A container according to the invention in certain instances may be a vial, an ampoule, a syringe, capsule, tablet or a tube. In some cases, the isolated *Mycobacterium* may be lyophilized and formulated for re-suspension prior to administration. However, in other cases, the mycobacteria are suspended in a volume of a pharmaceutically acceptable liquid. In some of the most preferred embodiments there is provided a container comprising a single unit dose of mycobacteria suspended in pharmaceutically acceptable carrier wherein the unit dose comprises about $1 \times 10^6$ to about $1 \times 10^{10}$ mycobacteria. In some very specific embodiments the liquid comprising suspended mycobacteria is provided in a volume of between about 0.1 ml and 10 ml, or about 0.5 ml and 2 ml. It will further be understood that in certain instances a composition comprising mycobacteria in a containment means is frozen (i.e. maintained at less than about zero degrees Celsius). The foregoing compositions provide ideal units for applications described herein.

Embodiments discussed in the context of a methods and/or composition of the invention may be employed with respect to any other method or composition described herein. Thus, an embodiment pertaining to one method or composition may be applied to other methods and compositions of the invention as well.

In some cases attenuated mycobacteria is administered to specific sites on or in a subject. For example, the mycobacterial compositions according to the invention may be administered adjacent to lymph nodes. Thus, in certain instances, sites of administration of a mycobacterial composition may be near the posterior cervical, tonsillar, axillary, inguinal, anterior cervical, sub-mandibular, sub mental or superclavicular lymph nodes. Such sites of administration may be on the right side, on the left side, or on both sides of the body. In certain very specific embodiments, mycobacterial compositions are delivered close to the axillary, cervical and/or inguinal lymph nodes. For example, a dosage of the mycobacteria may distribute into tissues adjacent to the right and left axillary lymph node and the right and left inguinal lymph nodes.

In a very specific embodiment a dosage of mycobacteria is administered to a subject by intradermal injection wherein the dosage is distributed to the axillary and inguinal on both sides of the body and wherein there are two injections (i.e. two wheals) at each site.

In some further embodiments of the invention, methods of the invention involve the administration of 2, 3, 4, 5, 6, 7, 8, 9, 10 or more doses of mycobacteria separated by a period of one day or more. In certain preferred embodiments such separate doses will be separated by several days, one week, two weeks, one month or more. For example, methods according to the invention may comprise administering 1 to 5 doses of mycobacteria over a period of three weeks or more. In yet further embodiments, methods of the invention comprise administering 1 to 5, 1 to 4, 1 to 3, 1 to 2 or 2 doses of mycobacteria over a period of about three weeks. Each dose administered may be the same or different dosage relative to a previous or subsequent dose administration. For example, in certain cases, it is preferred that a dosage of mycobacteria is lower than any dosage that was previously administered. Thus, in some specific cases, a dose of mycobacteria will be administered at about half of the dosage that was administered in any previous treatment. Such methods may be preferred in certain instances where the subject's immune response to the mycobacteria is greater during subsequent therapies. Thus in certain cases, the isolated *Mycobacterium* may be administered a minimal number of times for example, in less than 10, 9, 8, 7, 6, 5, 4, 3 or fewer separate dosage administrations. In some cases the mycobacterial composition is administered twice.

Mycobacterial compositions according to the invention will comprise an effective amount of mycobacteria typically dispersed in a pharmaceutically acceptable carrier. The phrases "pharmaceutical or pharmacologically acceptable" refers to molecular entities and compositions that do not produce an adverse, allergic or other untoward reaction when administered to a animal, such as, for example, a human, as appropriate. The preparation of an pharmaceutical composition that contains mycobacteria will be known to those of skill in the art in light of the present disclosure, as exemplified by Remington's Pharmaceutical Sciences, 18th Ed. Mack Printing Company, 1990, Moreover, for animal (e.g., human) administration, it will be understood that parenteral preparations should meet sterility, pyrogenicity, general safety and purity standards. A specific example of a pharmacologically acceptable carrier as described herein is borate buffer or sterile saline solution (0.9% NaCl).

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavouring agents, dyes, such like materials and combinations thereof, as would be known to one of ordinary skill in the art (see, for example, Remington's Pharmaceutical Sciences, 18th Ed. Mack Printing Company, 1990, pp. 1289-1329).

In a preferred embodiment, the isolated *Mycobacterium* is administered via a parenteral route selected from subcutaneous, intradermal, subdermal, intraperitoneal, intravenous, intravesicular injection or orally. Intradermal injection enables delivery of an entire proportion of the mycobacterial composition to a layer of the dermis that is accessible to immune surveillance and thus capable of electing appropriate immune response at local lymph nodes.

The invention is further described with reference to the following non-limiting Examples.

EXAMPLE

Summary

In an experimental model where mice are subjected to a stressful situation which results in some of the behavioural symptoms seen in PTSD, pre-treatment with *M. vaccae* decreases reactive emotional coping behaviours. Mice placed in a colony with a dominant aggressive male display behaviour reflective of the stress faced. These mice show, for example, increased submissive upright posture and increased avoidance behaviour. Treatment with *M. vaccae* decreases these behaviours and actually increased the percentage of proactive behaviour toward the dominant mouse at any time point recorded. These improved coping strategies in the face of a stressor, as would be seen in PTSD, were also observed in other tests of anxiety-related behaviour and social anxiety. Indeed, mice treated with *M. vaccae* showed reduced anxiety-related behaviour, indicated by increased time spent on the open arms of a maze compared with vehicle-treated mice. *M. vaccae* treatment also prevented lack of social preference in a social preference/avoidance test. Interestingly, Brain Tryptophan Hydroxylase 2 mRNA expression was significantly increased in the rostral dorsal raphe nucleus of *M. vaccae* pre-immunized mice. This is relevant in coping strategies in the face of stressors as the dopaminergic neurons in this area of the brain have been implicated in reward pathways. Hence, it is possible that *M. vaccae* treated animals expect a positive effect and therefore this bias diminishes the stress of adverse outcomes.

Similarly in a mouse model which exacerbates further the inflammatory response associated with PTSD, mice treated with *M. vaccae* showed an improved balance between inflammatory and anti-inflammatory response as shown by reduced levels of IL-6 and increased levels of IL-10, respectively, compared to vehicle-treated mice during DSS-induced colitis.

Materials and Methods
Animals

C57BL/6 male mice (19-22 g) housed in groups of 4-5 mice in polycarbonate cages (W×L×D: 27 cm×15 cm×42 cm) were treated with *M. vaccae* or vehicle (VEH) control. Briefly, mice were injected s.c. with *M. vaccae* [n=48; 0.1 mg whole cell heat-killed *M. vaccae* (NCTC11659) suspension of 10 mg/ml solution diluted to 1 mg/ml in 100 µl sterile borate-buffered saline (BBS)] or VEH (n=48; 100 µl of BBS) on days −21, −14, and −7. Upon the last injection mice were individually-housed in polycarbonate cages (W×L×D: 21 cm×14 cm×27 cm) for one week before initiation of assessment. All experimental protocols were approved by the Committee on Animal Health and Care of the local government, and performed according to international guidelines on the ethical use of animals.

Chronic Subordinate Colony Housing (CSC) Paradigm

Four experimental CSC mice were housed together with a larger dominant male (30-35 g; obtained from the mating of a high anxiety-related behaviour female with a C57BL/6 male) for 19 consecutive days, in order to induce chronic psychosocial stress as previously described[1,2]. To avoid habituation during the chronic stressor exposure, each larger male was replaced by a novel larger male on days 8 and 15 at 1000 h. Briefly, mice were kept under standard laboratory conditions (12-h light/dark cycle, lights on at 0600 h, 22° C., 60% humidity) with tap water and standard mouse diet ad libitum. The behaviour of all mice (CSC *M. vaccae*- and VEH-treated and dominant males) was recorded for 1 h on days 1, 8, and 15 in the morning (1000 h-1100 h; immediately after formation of the CSC colonies). Agonistic behaviour was analyzed in terms of proactive emotional coping behaviours (attacking, chasing, and mounting) and reactive emotional behaviours (flight, avoiding, defensive upright behaviour, attacks received, and mounts received).

Social Preference/Avoidance Test (SPAT)

The effects of *M. vaccae* treatment on social avoidance/anxiety behaviour were determined in the SPAT test. All experimental mice (VEH-SHC; VEH-CSC; *M. vaccae*-SHC; *M. vaccae*-CSC) were tested in the SPAT test as previously described[3,4] on day 21 between 0700 h-1200 h. Briefly, individual mouse were placed into the SPAT box (W×L×D: 27 cm×45 cm×27 cm; light intensity: 10-40 lux) for 30 seconds to allow familiarization before a small empty wire mesh cage (W×L×D: 6.5 cm×10 cm×5 cm) was introduced for 150 seconds. The empty cage was then removed and an identical cage containing an unfamiliar male mouse was introduced for a further 150 s. Total distance traveled and time spent in the 8-cm broad contact zone around the wire mesh cage was recorded. Behaviour during exposure to a novel object gives an indication of general anxiety. Behaviour during exposure to an unfamiliar mouse gives an indication of social avoidance.

Elevated Plus-Maze (EPM) Test

Upon completion of the SPAT test, the effects of *M. vaccae* treatment on anxiety-related behaviour were assessed in the EPM test. All experimental mice (VEH-SHC; VEH-CSC; *M. vaccae*-SHC; *M. vaccae*-CSC) were exposed to the EPM test for 5 minutes on day 22 between 0700 h-1200 h with 130 lux on the open and 30 lux on the closed arms of the maze as previously described. The maze, elevated 130 cm above the floor consists of two open and two closed arms (6 cm×30 cm, each) radiating from a central platform (6 cm×6 cm) to form a plus-shaped figure. Each individual mouse was placed on the central platform facing a closed arm. The time spent on the open and closed arms was recorded. The number of entries into the closed arms of the maze was taken as an indicator of locomotor activity.

Induction of DSS Colitis and Assessment of Severity

After termination of EPM testing, all experimental mice (VEH-SHC; VEH-CSC; *M. vaccae*-SHC; *M. vaccae*-CSC) received 1% dextran sulfate sodium (DSS) in their drinking water for one week starting on day 22 and were killed between 0800 h-1100 h of day 29 for assessment of colitis severity, as previously described[4,5]. Briefly, the colon of all experimental mice was removed, cleaned and histological damage score determined. Mesenteric lymph nodes cells were harvested and stimulated in culture for cytokine secretion measurement.

Treatment with *M. vaccae* Improves Coping Behaviour in the Face of a Stressor

The effects of *M. vaccae* treatment on general and social anxiety in CSC and SHC mice, *M. vaccae* and VEH-treated mice were determined. Treatment with *M. vaccae* decreases submissive and avoidance behaviour. In particular, pairwise comparisons revealed that *M. vaccae*-treated mice displayed significantly fewer submissive upright postures, received significantly fewer attacks and displayed fewer flight behaviours compared to VEH-treated mice on Day 1 ($p<0.001$; $p<0.001$; $p=0.005$). Moreover, pairwise comparisons showed that *M. vaccae*-treated mice displayed significantly fewer avoiding behaviours compared to VEH-treated mice on Day 1 ($p=0.023$) and on Day 15 ($p=0.011$). Pairwise comparisons revealed that *M. vaccae*-treated mice displayed significantly fewer mounts received compared to VEH-treated mice on Day 15 ($p=0.019$), but not on Day 1 or Day 8. The percentage of *M. vaccae*-treated mice showing proactive behaviour was significantly higher compared to the percentage of VEH-treated mice (83% vs 35%; $p=0.001$; FIG. 1A). Moreover, when a total dominance index was calculated (subtracting proactive from reactive behaviour), *M. vaccae*-treated mice showed a significantly increased total dominance index ($p=0.005$; FIG. 1B).

Social Preference/Avoidance Test (SPAT)

Figure 2:
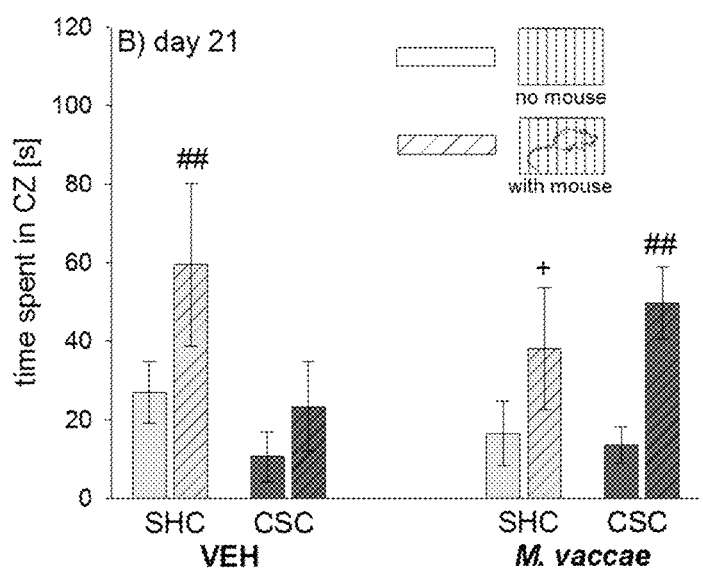
FIG. 2 shows that treatment with *M. vaccae* prevents CSC-induced lack of social preference in the SPAT test.

Time spent in the contact zone was significantly dependent on the presence of a stimulus (mouse in the small wire mesh cage) ($p<0.001$; FIG. 2). Post hoc analysis revealed that the time spent in the social (mouse inside the cage) compared with the non-social (no mouse in the cage) contact zone was significantly increased in the VEH-SHC ($p=0.004$) and the *M. vaccae*-CSC ($p=0.002$) group, and approached significance in the *M. vaccae*-SHC group ($p=0.064$). This effect was absent in the VEH-CSC group. This indicates that treatment with *M. vaccae* prevents CSC-induced lack of social preference. Importantly, total distance travelled was comparable among all treatment groups.

Elevated Plus-Maze (EPM) Test

Figure 3:
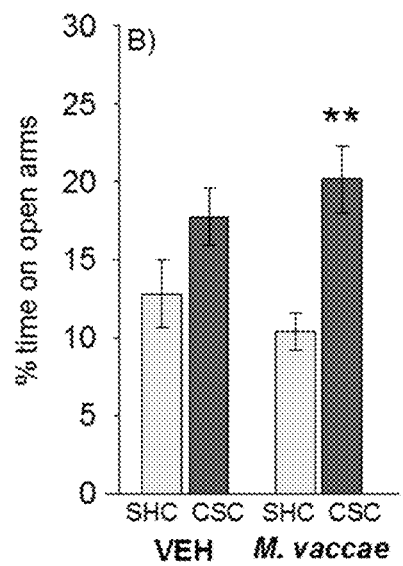
FIG. 3 shows that treatment with *M. vaccae* has anti anxiolytic properties in the EPM test.

Statistical analysis revealed that the percentage of time mice spent on the open arms was significantly increased in *M. vaccae*-treated CSC mice compared with respective SHC mice ($p=0.002$; FIG. 3). This indicates that treatment with *M. vaccae* has anti-anxiolytic properties.

Figure 4:
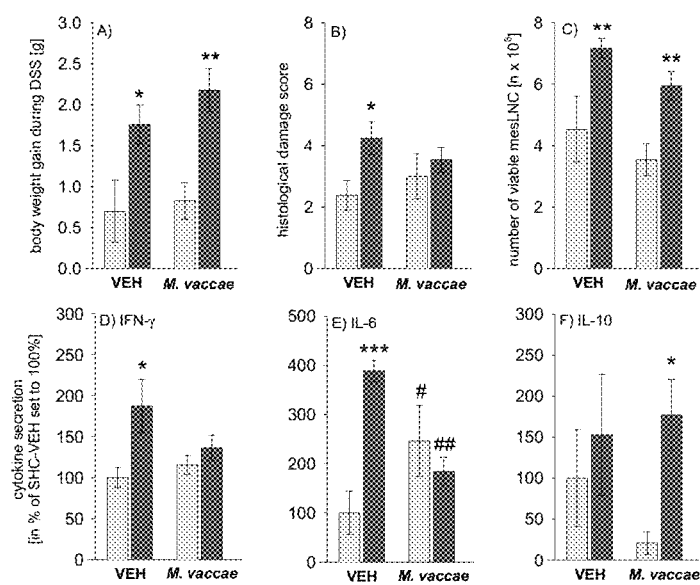
FIG. 4 shows the effects of *M. vaccae* pre-immunisation on CSC-induced aggravation on DSS-induced colitis.
Figure 5:
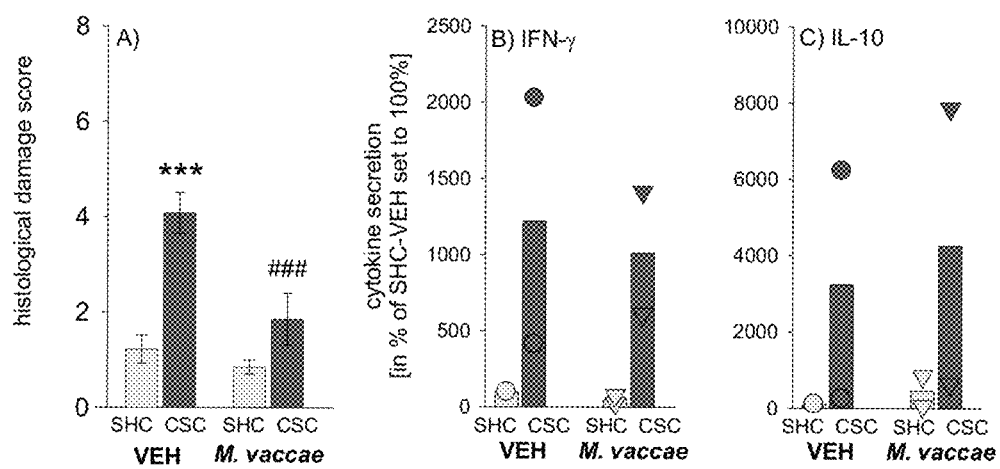
FIG. 5 shows the effect of pre-immunisation on the histological damage caused by CSC housing, as well as the effect on the ratio of inflammatory to regulatory cytokines.

Preimmunization with *M. vaccae* Ameliorated CSC-Induced Aggravation of DSS-Induced Colitis The effect of *M. vaccae* preimmunization on CSC-induced aggravation of DSS-induced colitis was determined (FIG. 4). CSC compared with SHC exposure aggravated the histological damage score in VEH-treated mice ($p=0.041$). *M. vaccae* treatment prevented the increase in the damage score (FIG. 4B). Moreover, *M. vaccae* treatment prevented the CSC-induced increase in the pro-inflammatory cytokines IFN-γ ($p=0.014$; FIG. 4D) and IL-6 ($p=0.001$; FIG. 4E) secretion. Furthermore, *M. vaccae*-treated CSC mice secreted elevated concentrations of IL-10 compared with respective SHC mice ($p=0.036$; FIG. 4F), an effect that was absent in VEH-treated mice.

REFERENCES

1. Reber S O, Birkeneder L, Veenema A H, Obermeier F, Falk W, Straub R H, Neumann I D. Adrenal insufficiency and colonic inflammation after a novel chronic psychosocial stress paradigm in mice: implications and mechanisms. Endocrinology 2007; 148:670-82.
2. Schmidt D, Reber S O, Botteron C, Barth T, Peterlik D, Uschold N, Männel D N, Lechner A. Chronic psychosocial stress promotes systemic immune activation and the development of inflammatory Th cell responses. Brain, Behavior and Immunity 2010; 24:1097-1104.
3. Haller J, Bakos N. Stress-induced social avoidance: A new model of stress-induced anxiety? Physiology & Behavior 2002; 77:327-332.
4. Reber S O, Obermeier F, Straub R H, Falk W, Neumann I D. Chronic intermittent psychosocial stress (social defeat/overcrowding) in mice increases the severity of an acute DSS-induced colitis and impairs regeneration. Endocrinology 2006; 147:4968-4976.
5. Reber S O, Obermeier F, Straub R H, Veenema A H, Neumann I D. Aggravation of DSS-induced colitis after chronic subordinate colony (CSC) housing is partially mediated by adrenal mechanisms. Stress 2008; 11:225-234.

The invention claimed is:

1. A method of treating or immunizing against at least one sign or symptom of post-traumatic stress disorder (PTSD) in a subject in need thereof, comprising administering a therapeutically effective amount of non-pathogenic heat-killed Mycobacterium vaccae to the subject.

2. The method of claim 1, wherein the Mycobacterium vaccae is a rough variant.

3. The method of claim 1, wherein the Mycobacterium vaccae is in the form of a vaccine composition optionally comprising an adjuvant.

4. The method of claim 1, wherein the subject is a member of the military.

5. The method of claim 1, wherein the Mycobacterium vaccae is administered in repeat doses.

6. The method of claim 1, wherein the Mycobacterium vaccae is administered in a unit dose comprising an effective amount of non-pathogenic heat-killed Mycobacterium vaccae from $10^7$ to $10^9$ cells.

7. The method of claim 1, wherein the Mycobacterium vaccae is formulated for administration via the parenteral, oral, sublingual, nasal or pulmonary route.

8. The method of claim 1, wherein the Mycobacterium vaccae is formulated for administration via the oral route.

9. The method of claim 7, wherein the parenteral route is selected from subcutaneous, intradermal, subdermal, intraperitonal, intravenous, or intravesicular injection.

10. The method of claim 1, wherein the method immunizing against at least one sign or symptom of post-traumatic stress disorder wherein the sign or symptom is selected from disorganized or agitated behaviour, problems with pain perception and pain tolerance, headache, difficult falling or staying asleep, repetitive play that expresses aspects of the trauma, frightening dreams which lack recognizable content, and trauma-specific re-enactment.

11. The method of claim 1, wherein the method immunizing against at least one symptom cluster of post-traumatic stress disorder wherein the symptom cluster is selected from re-experiencing/intrusion, avoidance/numbing, and hyperarousal.

12. The method of claim 11, wherein the subject is a military employee.

* * * * *